United States Patent [19]
Oikawa

[11] Patent Number: 4,847,363
[45] Date of Patent: * Jul. 11, 1989

[54] PHYSIOLOGICALLY ACTIVE GLYCOPROTEIN AND PROCESS FOR PRODUCTION THEREOF

[75] Inventor: Taneaki Oikawa, Yamagata, Japan

[73] Assignee: Bio Science Laboratory, Yamagata, Japan

[*] Notice: The portion of the term of this patent subsequent to Jan. 31, 2006 has been disclaimed.

[21] Appl. No.: 192,173

[22] Filed: May 10, 1988

Related U.S. Application Data

[63] Continuation of Ser. No. 854,470, Apr. 22, 1986, Pat. No. 4,801,689.

[30] Foreign Application Priority Data

Jul. 12, 1985 [JP]    Japan ................................ 60-152466

[51] Int. Cl.⁴ ............................................. C07K 15/14
[52] U.S. Cl. .................................. 530/395; 530/397; 530/413; 530/851; 530/853
[58] Field of Search .................... 514/8; 530/395, 397, 530/413, 851, 850

[56] References Cited

U.S. PATENT DOCUMENTS 4,430,428  2/1984  Fraser et al. ........................ 435/68
4,524,027  6/1985  Bohn ............................. 530/413 X
4,558,035 12/1985  Johnson ......................... 530/397 X

OTHER PUBLICATIONS

Gamete Research, 1:265–267 (1978), Oikawa.
Gamete Research, 3:217–231 (1980), Gwatkin.
Biochemistry, 2:356–365 (1980), Dunbar.
Biology of Reproduction 30:435–444 (1984), Drell.
Biology of Reproduction, 30: 445–457 (1984), Drell.
Biology of Reproduction, 32: 619–630 (1985), Dunbar.
Modern Cell Biology, 3: 77–111 (1984), Dunbar.
Biology of Reproduction, 24: 1111–1124 (1981), Dunbar.

*Primary Examiner*—Howard E. Schain
*Attorney, Agent, or Firm*—Wegner & Bretschneider

[57] ABSTRACT

A new glycoprotein ZP-0 originating from the oviduct of a mammal having a molecular weight of about 200,000 to 240,000, as determined by SDS-polyacrylamide gel density-gradient electrophoresis having an isoelectric point of about 4 to 6.2, as determined by isoelectric focusing, containing no sub-fragments, as determined by SDS-disk electrophoresis, forming a carbamylation train in two-dimensional electrophoresis (isoelectric focusing, and SDS-polyacrylamide gel density-gradient electrophoresis, and facilitating species-specific bonding of sperm to zonae pellucidae; and a process for production of the above-mentioned glycoprotein comprising, preparing oviduct from a mammal, homogenating the oviduct optionally with a buffer, to obtain a homogenate, obtaining a liquid containing the glycoprotein from the homogenate, adsorbing the glycoprotein onto lectin immobilized on an insoluble support, liberating the glycoprotein from the support, and recovering the glycoprotein.

2 Claims, 1 Drawing Sheet

PHYSIOLOGICALLY ACTIVE GLYCOPROTEIN AND PROCESS FOR PRODUCTION THEREOF

This application is a continuation of Ser. No. 854,470, filed Apr. 22, 1986, now U.S. Pat. No. 4,801,689.

BACKGROUND OF THE INVENTION

1. Field of the Invention

The present invention relates to a glycoprotein facilitating species-specific bonding of sperm to zonae pellucidae, and a process for production of the glycoprotein.

2. Description of the Related Art

For fertilization in mammals, sperm must reach the zonae pellucidae forming the outer membrane of the ovum. The zonae pellucidae is considered to play an important role, such as inter-species recognition and the rejection of polyspermy to establish monospermy, etc., during fertilization. However, substances involved in such processes are still not entirely clarified. The present inventors developed a method for the preparation of a large amount of mammalian ovum by an experimental system using pig ovaries, *Gamete Res.* 1, 265–267 (1978). This method was then modified by Dunber, B. S. et al., *Biochemistry*, 2, 356–365 (1980), and Gwatkin, R. B. L. et al, Gamete Res., 3, 217–231, (1980). Using this modification, Dunber, B. S. et al, *Biol. Reprod.*, 24, 1111–1124 (1981) found that the zonae pellucidae of an immature ovum from pigs and rabbits contains three kinds of glycoprotein, designated as ZP-1, ZP-2, and ZP-3, respectively. However, the composition of the substances in the zonae pellucidae of a matured ovum, which directly receive the sperm, has not been clarified.

SUMMARY OF THE INVENTION

Therefore, an object of the present invention is to provide a new glycoprotein, which is thought to play an important role during fertilization. The present glycoprotein has the following properties:

(1) originating from the oviduct of a mammal;
(2) having a molecular weight of about 200,000 to 240,000 as determined by SDS-polyacrylamide gel density-gradient electrophoresis;
(3) having an isoelectric point of about 4 to 6.2, as determined by isoelectric focusing;
(4) containing no sub-fragments, as determined by SDS-disk electrophoresis;
(5) forming a carbamylation train in two-dimensional electrophoresis (isoelectric focusing and SDS-polyacrylamide gel density-gradient electrophoresis); and
(6) facilitating the species-specific bonding of sperm to the zonae pellucidae.

Moreover, the present invention provides a process for the production of the above-mentioned glycoprotein, comprising:

(1) preparing oviduct from a mammal;
(2) homogenating the oviduct optionally with a buffer to obtain a homogenate;
(3) obtaining a liquid containing the glycoprotein from the homogenate;
(4) absorbing the glycoprotein onto lectin immobilized on an insoluble support;
(5) liberating the glycoprotein from the support; and
(6) recovering the glycoprotein.

DESCRIPTION OF THE PREFERRED EMBODIMENT

Figure 1:
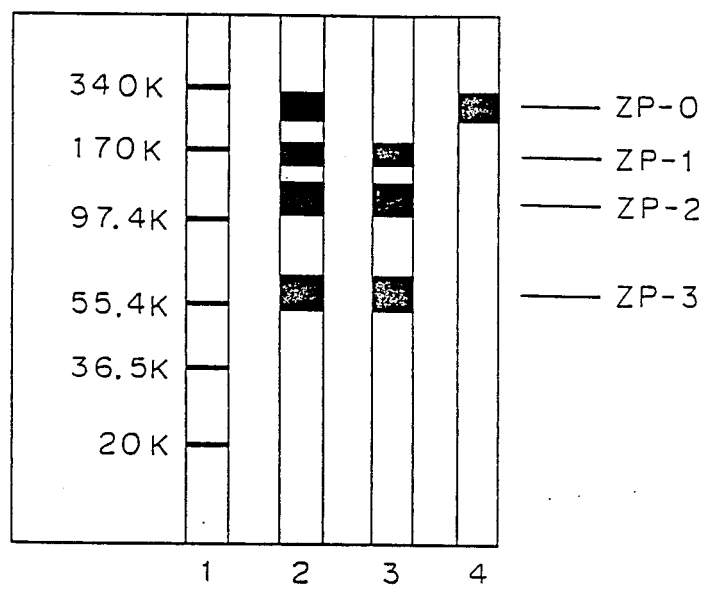
FIG. 1 represents an electrophoresis pattern of a glycoprotein preparation of the present invention, proteins derived from the zonae pellucidae of an immature ovum, and proteins derived from the zonae pellucidae of a matured ovum, wherein ZP-0 is the present glycoprotein, and ZP-1 to ZP-3 are known components. All materials are derived from a hamster.

The present invention developed a method for recovering a large amount of ova from small experimental animals so as to make possible the analyzing of substances present in the zonae pellucidae of such small animals. On the basis of this method, the present inventor compared components present in the zonae pellucidae of an immature ovum and components present in the zonae pellucidae of a matured ovum, and found that the zonae pellucidae of the matured ovum contains, in addition to the above-mentioned ZP-1, ZP-2, and ZP-3, which are present also in the zonae pellucidae of the immature ovum, a new substance having a higher molecular weight. This substance is not found in the zonae pellucidae of the immature ovum.

The present inventor, moreover, studied the origin, biological functions, and physico-chemical properties of the substance, and found that the substance is secreted by epitherial cells existing along inner wall of the oviduct, and in the oviduct, is bounded to the ZP-2 component present in the zonae pellucidae of the ovum after ovulation to form a component in the zonae pellucidae of the matured ovum, which component plays an important role in the attaching of sperm to the zonae pellucidae during the fertilization process. Moreover, the present inventor found the substance in question is a new glycoprotein.

PREPARATION PROCESS

The glycoprotein of the present invention can be isolated from the oviduct of mammals including humans, monkeys, cattle, pigs, goats, sheeps, horses, dogs, cats, rats, mice, and hamsters, etc. Since the starting material, i.e., the removed oviduct, is accompanied by blood, fat, and other impurities, the ovaries are thoroughly washed with an appropriate solution which will not denature the target substance, for example, Ringer's solution, phosphate buffer, acetate buffer, or the like.

The washed material is then homogenized by a conventional mechanical means such as a commercially available homogenizer. During the procedure, to prevent denaturation of the target substance, preferably a buffer having a pH value of about 7.0 to 8.0, preferably 7.4, such as a phosphate buffer, acetate buffer, or the like, is added to the washed material at a two to six times volume, for example, four times by volume of the washed material. The homogenation is preferably carried out at a lower temperature, for example, at a temperature lower than 5° C., to prevent denaturation of the target substance. The homogenation provides a pasty homogenate.

The homogenate is then subjected to a conventional separating means such as centrifuging, to separate a supernatant containing the target substance and a precipitate. Alternatively, the homogenate is filtered to obtain a filtrate containing the target substance. The supernatant or filtrate thus obtained contains, in addition to the target substance, water soluble compounds, fine particulate impurities, cell debris, fat particles, and the like.

Therefore, the supernatant or filtrate is preferably further treated to eliminate the above-mentioned impurities. For example, the supernatant or filtrate is filtered through a membrane filter which does not pass substances having a relatively high molecular weight, for example, a Toyo TM-4 membrane filter, to obtain a filtrate containing no particulate impurities. Alternatively, the supernatant or filtrate is subjected to a stronger centrifugation, such as ultracentrifugation.

The supernatant or filtrate thus obtained contains, in addition to the target substance, low molecular compounds, such as sugars, inorganic salts, and proteins having a relatively low molecular weight, therefore, such impurities are preferably eliminated. For this purpose, the supernatant or filtrate is preferably filtered through a membrane filter which does not pass substances having a molecular weight of more than 200,000 Dalton. An example of such a filter is a Toyo UK-200 membrane filter.

Next, the fraction thus obtained, containing substances having a molecular weight of more than about 200,000 Dalton, is subjected to an affinity chromatography using lectin immobilized on an insoluble support to purify the target substance. Lectin includes concanavalin A, *Solanum tuherosum* lectin, *Ricinus communis* I lectin, and the like. Insoluble support includes Sepharose, polyacrylamide beads, or agar beads. For the present process, concanavalin A—Sepharose-4D is typically used. For example, concanavalin A—Sepharose-4D is filled to a column, and equilibrated with an acetate buffer such as a 100 mM acetate buffer (pH 6.0) containing 1M NaCl, 1 mM $CaCl_2$, 1 mM $MgCl_2$, and 1 mM $MgCl_2$. Next, the column is charged with the fraction containing the target substance in the above-mentioned buffer. During this procedure, the target substance of the present invention, i.e., a glycoprotein, is specifically adsorbed to the concunavalin A. The column is then thoroughly washed with the above-mentioned buffer to elute any non-adsorbed or unspecifically adsorbed substances. The target glycoprotein is then eluted with an eluent which is preferably the above-mentioned buffer containing additional 0.2 M D-glucose.

After the affinity purification, a substantially purified glycoprotein of the present invention is obtained. However, further purification and concentration are preferably carried out using a membrane filter, such as the above-mentioned Toyo UK-200 membrane filter.

After this final treatment, the glycoprotein of the present invention is obtained in a homogeneous form, as determined by SDS-polyacrylamide gel density-gradient electrophoresis (5–15%).

Properties of the glycoprotein of the present invention localization

The present glycoprotein is originally present in the oviduct of mammals, and secreted therefrom. The secreted glycoprotein is transferred to the zonae pellucidae of the ovum after ovulation, and is present therein as a component thereof.

Physico-chemical Properties (1) The substance is a glycoprotein. This is verified by noting that the substance specifically bonds to concanavalin A—Sepharose 4B.

(2) The substance has a molecular weight of about 200,000 to 240,000 Dalton, as determined by SDS-polyacrylamide gel density gradient electrophoresis.

(3) The substance has an isoelectric point of about 4 to 6.2, as determined by isoelectric focusing.

(4) The substance contains no sub-fragments, as tested by SDS-disk electrophoresis.

(5) The substance forms a carbamylation train in two-dimensional electrophoresis (isoelectric focusing and SDS-polycarylamide gel density-gradient electrophoresis).

Biological properties (1) The present substance bonds to a glycoprotein ZP-2 present in the zonae pellucidae, and facilitates the species-specific bonding of sperm to the zonae pellucidae.

(2) The substance acts as an antigen for the preparation of antibodies against the present substance.

As described above, since the glycoprotein of the present invention facilitates the species-specific bonding of sperm to the zonae pellucidae, it can be used as an active ingredient in pharmaceuticals, for the treatment of sterilitas, and an improvement of the fertilization rate in artificial fertilization and external fertilization.

Moreover, the glycoprotein of the present invention is useful as an antigen for the production of antibodies against the glycoprotein by B-lymphocytes. Therefore, it may be useful as an immunogen for immunizing an animal to produce antiserum, and for forming hybridoma which can produce a monochonal antibody. These antiserum and monoclonal antibodies would be useful for an artificial control of fertilization.

EXAMPLES

The present invention will now be further shown by, but is by no means limited to, the following examples.

Examples 0.4 g of oviduct was removed from hamsters, and the oviduct was washed thoroughly with Ringer's solution. The washed oviduct was added with 2 ml of phosphatebuffered saline pH 7.4, and completely homogenized with a homogenizer cooled with ice to obtain a homogenate paste. The homogenate was centrifuged at 20,000 Xg for 10 minutes to obtain 2 ml of a supernatant. The supernatant was filtered through a Toyo TM-4 membrane filter to obtain 1.8 ml of a filtrate. The filtrate was filtered with an ultrafiltration apparatus using a Toyo UK-200 memblane filter, which does not pass substances having a molecular weight of more than 200,000. The filtration was carried out by supplementing a 100 mM acetate buffer pH 6.0 containing 1 M NaCl, 1 nM $CaCl_2$, 1 mM $MgCl_2$ and 1 mM $MnCl_2$ to a fraction which cannot pass the filter, to exchange buffers. In such a manner, 0.1 ml of a fraction comprising the glycoprotein of the present invention was dissolved in the above-mentioned acetate buffer.

A concanavalin A—Sepharose 4B column ($\phi$25 mm, 50 mm) was equilibrated with the above-mentioned acetate buffer, and charged with the above-mentioned glycoprotein-containing fraction. The column was washed with the acetate buffer to eliminate nonspecifically-bonded substances. The washing procedure was continued until absorption of the elute at 280 mm decreased to 0.005. The column was then subjected to elution with the above-mentioned acetate buffer containing additional 0.2M D-glucose, to elute glycoprotein specifically-adsorbed on the column, to obtain fractions. Among these fractions, those which show more than 0.005 of adsorption at 28 mm were combined to obtain 15 ml in total of the elute.

The combined fraction was concentrated by ultrafiltration using a Toyo UK-200 membrane filter which does not pass substances having a molecular weight of more than 200,000. During the procedure, a phosphate-buffered physiological saline was supplemented to a fraction which cannot pass the filter to carry out concentration and sugar elimination, as well as simultaneously exchanging the buffer. In such a manner, 0.5 ml of a final fraction was obtained.

The fraction showed a glycoprotein corresponding to a molecular weight of 200,000 to 240,000 as a sole high molecular component, as determined by SDS-polycarylamide gel density gradient electrophoresis (5-15%).

FIG. 1 represents electrophoresis patterns of the glycoprotein preparation thus obtained (lane 4), a preparation from the zonae pellucidae of the ovum obtained from oviduct (matured ovum) (lane 2), and a preparation prepared from the zonae pellucidae of the ovum obtained from ovaries (immature ovum) (lane 3). Lane 1 represents bands of maker proteins. The preparation derived from the zonae pellucidae of the immature ovum contains ZP-1, ZP-2, and ZP-3 substances. The preparation derived from the zonae pellucidae of the matured ovum contains, in addition to the ZP-1, ZP-2, and ZP-3 substances, a ZP-0 substance which corresponds to the glycoprotein of the present invention.

For the present invention, the present glycoprotein was identified as follows; the first location of glycoproteins on an electrophoresis gel were confirmed by specific bonding of the glycoprotein with a conjugate consisting of fluorescein isothiocyatale (FITC) and BS lectin-1 (FITC-BS lectin-1 conjugate), and then the thus-identified glycoprotein was tested for bonding to the ovum.

EXAMPLE 2

Confirmation of Biological Activity

Sperm was obtained from a hamster, rat, and mouse, and the sperm was subjected to capacitation treatment according to a conventional procedure. On the other hand, ovum samples were obtained from the ovaries of a hamster rat, mouse, and pig. The ovum sample from the pig was divided into two portions, and one portion was mixed with the glycoprotein, prepared as described in Example 1. Another portion was used as a control. Three sperm samples prepared as above, and ovum samples prepared as above, were mixed to form 15 mixed samples. The mixed samples were tested for bonding of the sperm and ovum, by microscopy. The result are shown in the following table.

| Kind of ovum | Kind of sperm | | |
|---|---|---|---|
| | Hamster | Rat | Mouse |
| Hamster | + | − | − |
| Rat | − | + | − |
| Mouse | − | − | + |
| Pig (treated with the present glycoprotein) | + | − | − |
| Pig (not treated) | − | − | − |

In the table, + shows samples wherein the sperm bonds to the ovum, and − shows samples wherein the sperm does not bond to the ovum. In tests of combinations between the sperm and ovum of a hamster, rat, and mouse, respectively, the species-specificity between sperm and ovum was confirmed. Pig ovum not treated with the present glycoprotein was not bound by the sperm of a hamster, rat, and mouse. On the other hand, pig ovum treated with the present glycoprotein derived from a hamster was bound by the sperm to the ovum of a hamster. This confirms that the glycoprotein of the present invention facilitates species-specific bonding of the sperm to the ovum.

I claim:
1. A substantially purified glycoprotein having a molecular weight of about 200,000 to 240,000, as determined by SDS-polyacrylamide gel density-gradient electrophoresis, characterized by having been prepared by the process consisting essentially of:
 (1) preparing oviduct from a mammal;
 (2) homogenating the oviduct with a buffer to obtain a homogenate;
 (3) obtaining a liquid containing glycoprotein from the homogenate;
 (4) filtering said liquid through a filter which does not pass substances having a molecular weight of more than 200,000 Daltons to obtain a residual material containing said glycoprotein;
 (5) absorbing said glycoprotein onto lectin immobilized on an insoluble support;
 (6) liberating said glycoprotein from said support;
 (7) recovering said glycoprotein.
2. A glycoprotein according to claim 1, wherein said mammal is a hamster.

* * * * *